United States Patent [19]

Baldwin et al.

[11] Patent Number: 4,678,806
[45] Date of Patent: Jul. 7, 1987

[54] PRODRUGS OF ANTIHYPERCHOLESTEROLEMIC COMPOUNDS

[75] Inventors: John J. Baldwin, Gwynedd Valley; Wasyl Halczenko, Hatfield; George Hartman; Steven M. Pitzenberger, both of Lansdale, all of Pa.

[73] Assignee: Merck & Co., Inc., Rahway, N.J.

[21] Appl. No.: 902,895

[22] Filed: Sep. 2, 1986

[51] Int. Cl.⁴ .................. A61K 31/235; C07C 101/72
[52] U.S. Cl. ..................................... 514/539; 514/400; 514/419; 514/423; 514/533; 514/547; 548/342; 548/496; 548/532; 548/535; 560/16; 560/39; 560/40; 560/153; 560/169; 560/170; 562/426; 562/444; 562/445; 562/557; 562/559; 562/564; 562/567
[58] Field of Search ............... 548/342, 496, 532, 535; 560/16, 39, 40, 153, 169, 170; 562/426, 444, 445, 557, 559, 564, 567; 514/400, 419, 423, 533, 539, 547

[56] References Cited

U.S. PATENT DOCUMENTS

| | | | |
|---|---|---|---|
| 3,983,140 | 9/1976 | Endo et al. | 435/72 |
| 4,049,495 | 9/1977 | Endo et al. | 435/125 |
| 4,137,322 | 1/1979 | Endo et al. | 514/400 |
| 4,231,938 | 11/1980 | Monaghan et al. | 435/125 |
| 4,294,846 | 10/1981 | Albers-Schonberg et al. | 514/460 |
| 4,294,926 | 10/1981 | Monoghan et al. | 435/125 |
| 4,319,039 | 3/1982 | Albers-Schonberg | 435/125 |
| 4,323,648 | 4/1982 | Tanzawa et al. | 435/125 |
| 4,351,844 | 9/1982 | Patchett et al. | 514/460 |
| 4,375,475 | 3/1983 | Willard et al. | 514/460 |
| 4,459,422 | 7/1984 | Willard et al. | 560/59 |
| 4,517,373 | 5/1985 | Terahara et al. | 549/292 |

OTHER PUBLICATIONS

P. K. Banerjee, G. L. Amidon, *J. Pharm. Sci.*, 70, 1299-1303 (1981).
Z. M.-Eldien, A. Hussain, *J. Pharm. Sci.*, 72, 1093-1096 (1983).

*Primary Examiner*—James H. Reamer
*Assistant Examiner*—Bruce D. Gray
*Attorney, Agent, or Firm*—Joseph F. DiPrima; Michael C. Sudol, Jr.

[57] ABSTRACT

Prodrugs of 3-hydroxy-3-methylglutarylcoenzyme A (HMG-CoA) reductase inhibitors which are useful as antihypercholesterolemic agents and are represented by the following general structural formula (I):

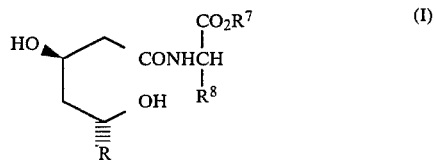

the amido ester moiety of which is in the L-configuration, and pharmaceutically acceptable salts thereof are disclosed.

21 Claims, No Drawings

PRODRUGS OF ANTIHYPERCHOLESTEROLEMIC COMPOUNDS

BACKGROUND OF THE INVENTION

Hypercholesterolemia is known to be one of the prime risk factors for ischemic cardiovascular disease, such as arteriosclerosis. To date, there is still no effective antihypercholesterolemic agent commercially available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG-CoA reductase. These agents include the natural fermentation products compactin and mevinolin and a variety of semi-synthetic and totally synthetic analogs thereof.

The naturally occurring compounds and their semi-synthetic analogs have the following general structural formulae:

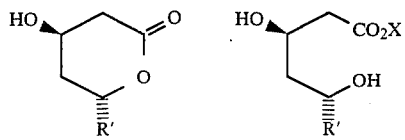

wherein
X is hydrogen, $C_{1-5}$alkyl or $C_{1-5}$alkyl substituted with a member of the group consisting of phenyl, dimethylamino or acetylamino;
R' is

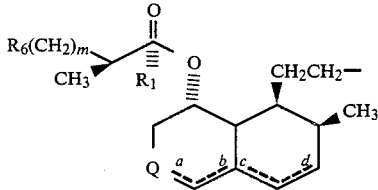

wherein
m is 1 to 5;
Q is

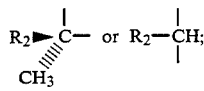

$R_2$ is hydrogen or hydroxy;
$R_1$ is hydrogen or methyl; and
$R_6$ is hydrogen, hydroxy or

a, b, c and d are single bonds, one of a, b, c and d is a double bond or a and c or b and d are double bonds provided that when a is a double bond, Q is

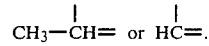

The totally synthetic antihypercholesterolemic compounds are disclosed in U.S. Pat. No. 4,375,475 and have the following general structural formulae:

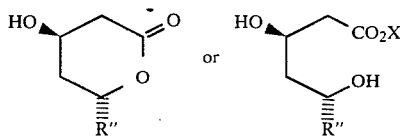

wherein R" is:

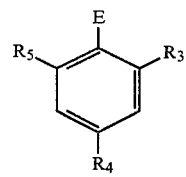

wherein:
E is $-CH_2-$, $-CH_2CH_2-$ or $-CH=CH-$;
$R_3$ and $R_4$ are independently $C_{1-3}$alkyl, fluoro, bromo or chloro; and
$R_5$ is phenyl, benzyloxy, substituted phenyl or substituted benzyloxy in which the phenyl group in each case is substituted with one or more substituents selected from $C_{1-3}$alkyl, fluoro, bromo or chloro.

SUMMARY OF THE INVENTION

This invention relates to novel compounds which are prodrugs of known HMG-CoA reductase inhibitors and which are bioconverted following systemic administration to useful antihypercholesterolemic agents. Specifically, the compounds of this invention include amido acid and amido ester derivatives of the ring opened form of compactin, mevinolin, CS514, the dihydro and tetrahydro analogs thereof and the totally synthetic HMG-CoA reductase inhibitors. Additionally, pharmaceutical compositions of these prodrugs, as the sole therapeutic agent, and in combination with bile acid sequestrants are disclosed.

DETAILED DESCRIPTION OF THE INVENTION

The specific prodrugs of this invention are the compounds represented by the following general structural formula (I):

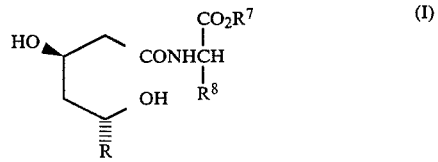

wherein R is selected from a group consisting of:
(a)

$$\underset{CH_3}{R^9(CH_2)_n}\overset{O}{\underset{R^1}{\|}}\text{—}\underset{A}{\overset{a}{\text{—}}}\underset{b}{\overset{O}{\|}}\underset{c}{\text{—}}\underset{d}{\text{—}}\underset{B}{\overset{CH_2CH_2—}{\underset{CH_3}{\|}}}$$

wherein:

n is 1 to 6;

$R^1$ is hydrogen or methyl;

$R^9$ is hydrogen, hydroxy or $$(C_{1-5}alkyl)\overset{O}{\overset{\|}{C}}O—;$$

A is $$R^2\text{—}\underset{CH_3}{\overset{|}{\underset{\|}{C}}}\text{— or } R^2\text{—}\overset{|}{\underset{|}{CH}},$$

in which $R^2$ is hydrogen or hydroxyl;

B is $$\overset{|}{-CHR^3},$$

in which $R^3$ is hydrogen or hydroxyl;

a, b, c and d represent single bonds, one of a, b, c and d represents a double bond or both a and c or both b and d represent double bonds, provided that when a is a double bond, A is $$\underset{CH_3}{\overset{|}{\underset{/}{C}}}\text{= or } \overset{|}{CH}=$$

and when d is a double bond, B is $$=\overset{|}{CH};$$

or (b)

[structure of substituted phenyl ring with E at top, $R^6$ at left, $R^4$ at right, $R^5$ at bottom]

wherein:

E is —CH$_2$—, —CH$_2$CH$_2$— or —CH=CH—;

$R^4$ and $R^5$ are independently $C_{1-3}$alkyl, fluoro, bromo or chloro; and $R^6$ is phenyl, benzyloxy, substituted phenyl or substituted benzyloxy in which the phenyl group in each case is substituted with one or more substituents selected from $C_{1-3}$alkyl, hydroxy-$C_{1-3}$alkyl, fluoro, bromo or chloro;

$R^7$ is hydrogen or $C_{1-8}$alkyl; and $R^8$ is $C_{1-8}$alkyl, hydroxy-$C_{1-8}$alkyl, phenyl-$C_{1-8}$alkyl, hydroxyphenyl-$C_{1-8}$alkylamido-$C_{1-8}$alkyl, $C_{1-8}$alkoxycarbonyl-$C_{1-8}$alkyl, imidazol-4-yl-$C_{1-8}$alkyl, $C_{1-8}$alkylthio-$C_{1-8}$alkyl, 2-(($C_{1-8}$alkoxycarbonyl)-pyrrolidin-4-yl)-$C_{1-8}$alkyl or indol-3-yl-$C_{1-8}$ alkyl;

the amido ester moiety of which is in the L-configuration and pharmaceutically acceptable salts of the compounds of the formula (I) wherein $R^7$ is hydrogen.

One embodiment of this invention are the compounds of the formula (I) wherein R is the group (b). Illustrative of this embodiment are the compounds wherein E is —CH=CH—; $R^4$ and $R^5$ are independently $C_{1-3}$alkyl and $R^6$ is substituted phenyl. More specifically, group (b) is:

[structure of biphenyl with F, three CH$_3$ groups, and propenyl substituent]

Exemplifying this embodiment are the class of compounds wherein $R^8$ is $C_{1-8}$alkyl and specifically:

(1) N-[7-(4'-fluoro-3,3',5-trimethyl-[1,1'-biphenyl]-2-yl)-3(R),5(R)-dihydroxy-1-oxo-6-hepten-1-yl]-L-leucine; and (2) methyl N-[7-(4'-fluoro-3,3',5-trimethyl-[1,1'-biphenyl]-2-yl)-3(R),5(R)-dihydroxy-1-oxo-6-hepten-1-yl]-L-leucinate.

A second class of compounds of this embodiment contains those compounds wherein $R^8$ is hydroxy-$C_{1-8}$alkyl and specifically:

(1) N-[7-(4'-fluoro-3,3',5-trimethyl-[1,1'-biphenyl]-2-yl)-3(R),5(R)-dihydroxy-1-oxo-6-hepten-1-yl]-L-serine; and (2) methyl N-[7-(4'-fluoro-3,3',5-trimethyl-[1,1'-biphenyl]-2-yl)-3(R),5(R)-dihydroxy-1-oxo-6-hepten-1-yl]-L-serinate.

A third class of compounds of this embodiment contains those compounds wherein $R^8$ is phenyl-$C_{1-8}$alkyl and specifically:

(1) N-[7-(4'-fluoro-3,3',5-trimethyl-[1,1'-biphenyl]-2-yl)-3(R),5(R)-dihydroxy-1-oxo-6-hepten-1-yl]-L-phenylalanine; and (2) methyl N-[7-(4'-fluoro-3,3',5-trimethyl-[1,1'-biphenyl]-2-yl)-3(R),5(R)-dihydroxy-1-oxo-6-hepten-1-yl]-L-phenylalanate.

A fourth class of compounds of this embodiment contains those compounds wherein $R^8$ is hydroxyphenyl-$C_{1-8}$alkyl and specifically, N-[7-(4'-fluoro-3,3',5-trimethyl-[1,1'-biphenyl]-2-yl)-3(R),5(R)-dihydroxy-1-oxo-6-hepten-1yl]-L-tyrosine.

A second embodiment of this invention are the compounds of the formula (I) wherein R is the group (a).

The pharmaceutically acceptable salts of this invention include those formed from cations such as sodium, potassium, aluminum, calcium, lithium, magnesium, zinc, and from bases such as ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compounds of this invention are conveniently prepared by opening of the parent lactone by a $C_{1-8}$alkyl ester of the appropriate L-amino acid or its corresponding acid salt according to the following synthetic pathway:

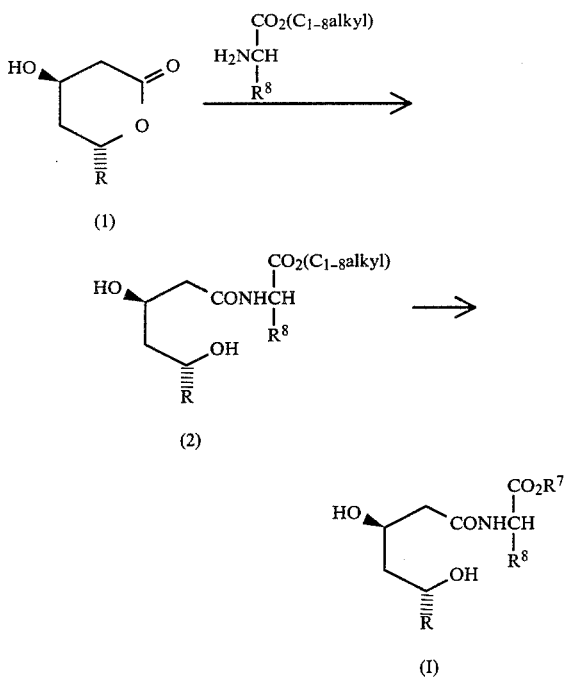

The compounds of the formula (1) are known in the art. When R is the group (a), the compounds of the formula (1) are compactin, mevinolin, CS514 and their dihydro and tetrahydro analogs which are readily available or may be prepared according to the fermentation procedures disclosed in U.S. Pat. Nos. 3,983,140; 4,049,495; 4,231,938; 4,294,846 and 4,517,373 and the hydrogenation procedures disclosed in U.S. Pat. No. 4,351,844. When R is the group (b), the compounds of the formula (1) are readily available by utilizing the procedures described in U.S. Pat. No. 4,375,475.

The compounds of the formula (1) are reacted with a $C_{1-8}$alkyl ester of the appropriate L-amino acid, as the acid addition salt in which the acid used is a protic acid such as hydrochloric acid, hydrobromic acid, hydroiodic acid, sulfonic acid, benzenesulfonic acid, toluenesulfonic acid, methanesulfonic acid and the like, in the presence of a base such as trialkylamine, specifically trimethylamine, triethylamine, pyridine, N,N-dimethylbenzylamine and the like, to afford the compounds of the formula (2). The compounds of the formula (2) are compounds of this invention wherein $R^7$ is $C_{1-8}$alkyl. To arrive at the compounds of this invention wherein $R^7$ is hydrogen, the compounds of the formula (2) are prepared by a controlled alkaline hydrolysis under mild conditions. Therefore, the compounds of the formula (2) are treated with a dilute alkali hydroxide such as sodium hydroxide, potassium hydroxide and the like, under aqueous conditions at low temperatures, such as −10° to 10° C. The resultant alkali salt is carefully acidified with a dilute protic acid to a pH of 4.

The compounds of this invention are useful as prodrugs of antihypercholesterolemic agents for the treatment of arteriosclerosis, hyperlipidemia, familial hyperchloesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 20 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The ability of the compounds of this invention to act as prodrugs of antihypercholesterolemic agents is demonstrated in a standard in vivo pharmacological assay in dogs.

Eight male beagle dogs weighing from 7.2–12.9 kilograms approximately 4–5 years old were fed a low cholesterol, semi-synthetic diet once a day in the morning in sufficient quantity to maintain a constant body weight. The animals were trained to consume their entire ration each day. Cholestyramine, 12 g, was administered daily in the diet. This amount routinely resulted in an average reduction in plasma total cholesterol of approximately 35%. Dogs were bled twice a week from the jugular vein and plasma cholesterol was determined after extraction and saponification by a colorimetric procedure (Liebermann Burchard). After the establishment of pretreatment plasma cholesterol levels, one or more dogs were treated with a daily dose of test compound mixed directly into the diet for 14 days.

Representative of the pharmacological activity of the compounds of this invention tabulated below are a number of compounds and the percentage decrease in cholesterol levels in dogs at specified dosages after 14 days of treatment.

| Compounds | | Dosage (mg/kg/day) | Percent Decrease in Plasma Cholesterol |
|---|---|---|---|
| $R^7$ | $R^8$ | | |
| H | $CH_2CH(CH_3)_2$ | 8 | 35 |
| $CH_3$ | $CH_2CH(CH_3)_2$ | 8 | 36 |
| H | $CH_2OH$ | 8 | 13 |
| $CH_3$ | $CH_2OH$ | 8 | 32 |
| $CH_3$ | $CH_2$—⌬ | 8 | 38 |
|  |  | 4 | 28 |
| H | $CH_2$—⌬—OH | 8 | 32 |

Included within the scope of this invention is the method of treating arteriosclerosis, familial hypercholesterolemia or hyperlipidemia which comprises administering to a subject in need of such treatment the compounds of formula (I) or pharmaceutical compositions thereof.

The following examples illustrate the preparation of the compounds of the formula (I) and their incorporation into pharmaceutical compositions and as such are not to be considered as limiting the invention set forth in the claims appended hereto.

EXAMPLE 1

Preparation of methyl
N-[7-(4'-fluoro-3,3',5-trimethyl-[1,1'-biphenyl]-2-yl)-3(R),5(S)-dihydroxy-1-oxo-6-hepten-1-yl]-L-phenylalanate (1)

To 5.32 g (15.0 mmol) 6(E)-[2-(4'-fluoro-3,3',5-trimethyl-[1,1'-biphenyl]-2-yl)-ethenyl]-3,4,5,6-tetrahydro-4(R)-hydroxy-2H-pyran-2-one [prepared according to U.S. Pat. No. 4,375,475] in 150 ml tetrahydrofuran (THF) was added 6.8 g (31.5 mmol) methyl-L-phenylalanine hydrochloride (2) and 3.19 g (31.5 mmol) triethylamine and the resulting solution was heated at reflux for 42 hours. The cooled reaction mixture was taken up in 300 ml diethyl ether, washed successively with 3×75 ml portions of $H_2O$, 30 ml 0.5N HCl, 50 ml $H_2O$, 50 ml saturated $NaHCO_3$ solution, 50 ml $H_2O$, brine and dried. Solvent removal in vacuo gave an oil which was purified by flash chromatography on silica gel eluting with 5% $CH_3OH/CHCl_3$ to give the desired compound as an oil. This was stirred overnight under hexane to afford the above-titled compound as a white solid, m.p. 87°–91° C. $^1H$ NMR ($CDCl_3$) δ 1.37 (m, 1H), 1.55 (m, 1H), 2.27 (d, 2H), 2.32 (m, 9H), 2.81 (d, 1H), 3.08 (dd, 1H), 3.17 (dd, 1H), 3.75 (s, 3H), 4.07 (m, 1H), 4.10 (d, 1H), 4.35 (m, 1H), 4.89 (dd, 1H), 5.37 (dd, 1H), 6.37 (d, 1H), 6.43 (d, 1H), 7.1 (m, 10H, aromatic).

Anal. Calc'd for $C_{32}H_{36}FNO_5$: C, 72.02; H, 6.80; N, 2.62; Found: C, 72.16; H, 6.99; N, 2.59.

EXAMPLE 2

Preparation of
N-[7-(4'-fluoro-3,3',5-trimethyl-[1,1'-biphenyl]-2-yl)-3R(S),5(S)-dihydroxy-1-oxo-6-hepten-1-yl]-L-phenylalanine (2)

To 0.107 g (0.2 mmol) of the compound from Example 1 in 1.5 ml of a 2:1 solution of dioxane:$H_2O$ cooled in an ice-bath, was added dropwise 0.2 ml of 1N NaOH solution over 5 minutes. After stirring at 0°–10° C. for 2 hours, the solution was concentrated in vacuo and this was taken up in 3 ml $H_2O$. This was washed with diethyl ether and then acidified with 3N HCl. The resulting white suspension was extracted with 3×5 ml $CH_2Cl_2$ and this was washed with brine and dried. Solvent removal gave the above-titled compound as a solid, m.p. 78°–80° C. $^1H$ NMR ($CDCl_3$) δ 1.34 (m, 1H), 1.51 (m, 1H), 2.25 (d, 2H), 2.32 (s, 9H), 3.05 (dd, 1H), 3.21 (dd, 1H), 4.04 (m, 1H), 4.30 (m, 1H), 4.80 (br m, 3H), 5.35 (dd, 1H), 6.40 (d, 1H), 6.67 (d, 1H), 7.1 (m, 11H, aromatic+$CO_2H$).

Anal. Calc'd for $C_{31}H_{34}FNO_5 \cdot 1.25H_2O$ C, 68.68; H, 6.79; N, 2.58; Found: C, 68.72; H, 6.51; N, 2.31.

EXAMPLE 3

Preparation of methyl
N-[7-(4'-fluoro-3,3',5-trimethyl-[1,1'-biphenyl]-2-yl)-3(R),5(S)-dihydroxy-1-oxo-6-hepten-1-yl]-L-leucinate (3)

The above-title compound was prepared in analogous fashion utilizing the general procedure of Example 1; m.p. 62°–65° C. $^1H$ NMR ($CDCl_3$) δ 0.94 (d, 6H), 1.40 (dt, 1H), 1.61 (m, 4H), 2.28 (d, 3H), 2.33 (s, 3H), 2.35 (s, 3H), 2.36 (m, 2H), 2.82 (d, 1H, 3.74 (s, 3H), 4.17 (m, 1H), 4.30 (d, 1H), 4.38 (m, 1H), 4.63 (m, 1H), 5.38 (dd, 1H), 6.32 (br d, 1H, NH), 6.44 (d, 1H), 6.90–7.12 (m, aromatic).

Anal. Calc'd for $C_{29}H_{38}FNO_5$: C, 69.71; H, 7.67; N, 2.80; Found: C, 69.71; H, 7.87; N, 3.01.

EXAMPLE 4

Preparation of
N-[7-(4'-fluoro-3,3',5-trimethyl-[1,1'-biphenyl]-2-yl)-3(R),5(S)-dihydroxy-1-oxo-6-hepten-1-yl]-L-leucine (4)

The above-titled compound was prepared in analogous fashion utilizing the general procedure of Example 2; m.p. 122°–124° C. $^1H$ NMR ($CDCl_3$) δ 0.95 (dd, 6H), 1.43 (dt, 1H), 1.66 (m, 4H), 2.28 (d, 3H), 2.33 (s, 3H), 2.34 (s, 3H), 2.37 (m, 2H), 4.17 (m, 1H), 4.38 (m, 1H), 4.56 (m, 1H), 5.38 (dd, 1H), 6.43 (d, 1H), 6.66 (br d, 1H), 6.91–7.11 (m, 5H, aromatic).

Anal. Calc'd for $C_{28}H_{36}FNO_5$: C, 69.25; H, 7.47; N, 2.89; Found: C, 69.34; H, 7.54; N, 3.00.

EXAMPLE 5

Preparation of methyl
N-[7-(4'-fluoro-3,3',5-trimethyl-[1,1'-biphenyl]-2-yl)-3(R),5(S)-dihydroxy-1-oxo-6-hepten-1-yl]-L-serinate (5)

The above-titled compound was prepared in analogous fashion utilizing the general procedure of Example 1; m.p. 125°–129° C. $^1H$ NMR ($CDCl_3$) δ 1.43 (dt, 1H), 1.58 (m, 1H), 2.28 (d, 3H), 2.33 s, 3H), 2.34 (s, 3H), 2.38 (m, 2H), 2.70 (br s, 1H), 2.80 (m, 1H), 3.80 (s, 3H), 3.97 (dd, 2H), 4.21 (m, 1H), 4.37 (br s, 1H), 4.38 (m, 1H), 4.68 (m, 1H), 5.38 (dd, 1H), 6.43 (d, 1H), 6.85 (br d, 1H), 6.91–7.10 (m, 5H, aromatic).

Anal. Calc'd for $C_{26}H_{32}FNO_6$: C, 65.94; H, 6.81; N, 2.96; Found: C, 65.84; H, 6.74; N, 2.92.

EXAMPLE 6

Preparation of
N-[7-(4'-fluoro-3,3',5-trimethyl-[1,1'-biphenyl]-2-yl)-3(R),5(S)-dihydroxy-1-oxo-6-hepten-1-yl]-L-serine (6)

The above-titled compound was prepared in analogous fashion utilizing the general procedure of Example 2; m.p. 149°–151° C. $^1H$ NMR ($CDCl_3$) δ 1.42 (m, 2H), 2.20 (br s, 5H), 2.28 (s, 3H), 2.32 (s, 3H), 3.62 (m, 2H), 3.84 (m, 1H), 4.09 (m, 1H), 4.28 (m, 1H), 4.70 (d, 1H), 4.75 (br s, 1H), 5.38 (dd, 1H), 6.27 (d, 1H), 6.88 (s, 1H), 7.03 (s, 1H), 7.05–7.20 (m, 3H, aromatic), 7.97 (d, 1H, NH), 12.55 (br, 1H, $CO_2H$).

Anal. Calc'd for $C_{25}H_{30}FNO_6$: C, 65.34; H, 6.58; N, 3.05; Found: C, 65.22; H, 6.68; N, 3.30.

EXAMPLE 7

Preparation of N-[3,3′,5-trimethyl-[1,1′-biphenyl]-2-yl)-3(R),5(S)-dihydroxy-1-oxo-6-hepten-1-yl]-L-tyrosine (7)

The above-titled compound was prepared in analogous fashion utilizing the general procedures in Examples 1 and 2; m.p. 154°–155° C. $^1$H MR (CDCl$_3$) δ 1.32 (m, 1H), 1.42 (m, 1H), 2.18 (d, 2H), 2.23 (s, 3H), 2.27 (s, 3H), 2.31 (s, 3H), 2.77 (dd, 1H), 2.89 (dd, 1H), 3.80 (m, 1H), 4.07 (m, 1H), 4.35 (dd, 1H), 4.64 (br s, 1H), 4.74 (d, 1H), 5.36 (dd, 1H), 6.25 (d, 1H), 6.63 (d, 2H), 7.10 (m, 8H, aromatic+OH), 8.04 (d, 1H), 9.19 (s, 1H, CO$_2$H).

Anal. Calc'd for C$_{31}$H$_{34}$FNO$_6$: C, 69.51; H, 6.40; N, 2.62; Found: C, 69.26; H, 6.65; N, 2.65.

EXAMPLES 8–20

The following compounds in Tables I and II are prepared according to the general procedures of Examples 1 and 2 utilizing the appropriate starting materials.

TABLE I

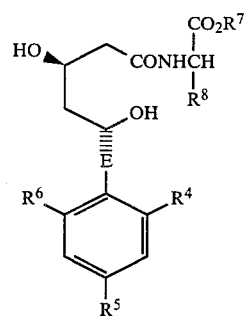

| Compound | E | R$^4$ | R$^5$ | R$^6$ | R$^7$ | R$^8$ |
|---|---|---|---|---|---|---|
| 8 | CH=CH | Et | Et | 3,5-di-CH$_3$-phenyl | Et | Me |
| 9 | CH=CH | iPr | iPr | 3,5-di-Cl-phenyl | n-Bu | —CH$_2$CH$_2$OH |
| 10 | CH$_2$CH$_2$ | Cl | Cl | phenyl-O— | H | —CH$_2$CH$_2$-phenyl |
| 10 | CH$_2$CH$_2$ | Cl | Cl | phenyl-O— | H | —CH$_2$CH$_2$-phenyl |
| 11 | CH$_2$CH$_2$ | Me | Me | 2-F,3-HOCH$_2$-phenyl | H | —CH$_2$-phenyl |
| 12 | CH$_2$CH$_2$ | Me | Me | 2-F,3-CH$_3$-phenyl | Me | —CH$_2$-phenyl |

TABLE I-continued

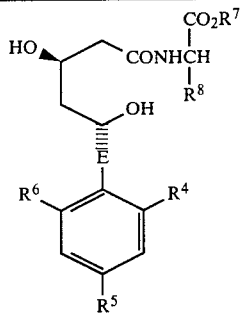

| Compound | E | R⁴ | R⁵ | R⁶ | R⁷ | R⁸ |
|---|---|---|---|---|---|---|
| 13 | $CH_2$ | Et | Et |  | n-Hex | $CH_2CH(CH_3)_2$ |

TABLE II

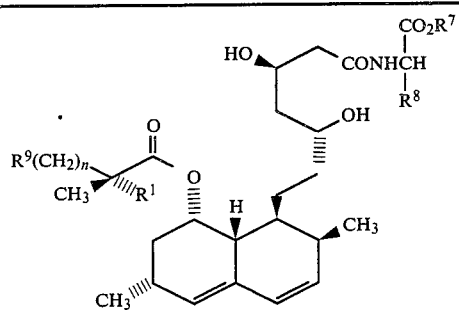

| Compound | n | R¹ | R⁷ | R⁸ | R⁹ |
|---|---|---|---|---|---|
| 1 | | Me | Me | H 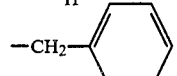 —$CH_2$— ⌬ | |
| 15 | 1 | H | H | 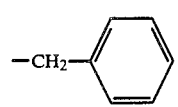 —$CH_2$— ⌬ | OH |
| 16 | 5 | Me | Me | —$CH_2CH(CH_3)_2$ | $\underset{\|}{\overset{O}{O-C-CH_3}}$ |
| 17 | 5 | Me | Me | —$CH_2OH$ | |
| 18 | 3 | Me | H | 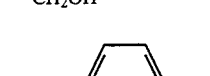 —$CH_2$—⌬—OH | OH |
| 19 | 3 | Me | H | 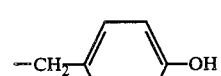 —$CH_2$—⌬—OH | H |
| 20 | 1 | H | Me | —$CH_2CH(CH_3)_2$ | $\underset{\|}{\overset{O}{O-C-CH_2CH_3}}$ |

EXAMPLE 21

As a specific embodiment of a composition of this invention, 20 mg of the compound of Example 1 is formulated with sufficient finely divided lactose to provide a total amount of 580 to 590 mg to fill a size 0 hard gelatin capsule.

What is claimed is:

1. A compound represented by the general structural formula (I):

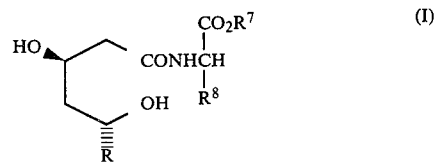

(I)

wherein R is selected from a group consisting of:

(a)

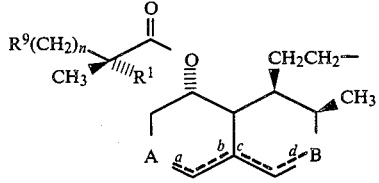

wherein
n is 1 to 6;
$R^1$ is hydrogen or methyl;
$R^9$ is hydrogen, hydroxy or

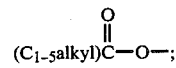
$(C_{1-5}alkyl)\overset{O}{\underset{\|}{C}}-O-$;

A is

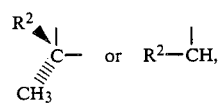

in which $R^2$ is hydrogen or hydroxyl;
B is

in which $R^3$ is hydrogen or hydroxyl;

a, b, c and d represent single bonds, one of a, b, c and d represent a double bond or both a and c or both b and d represent double bonds, provided that when a is a double bond, A is

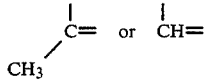

and when d is a double bond, B is

or (b)

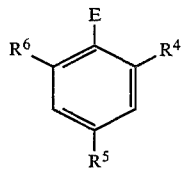

wherein:

E is $-CH_2-$, $-CH_2CH_2-$ or $-CH=CH-$;

$R^4$ and $R^5$ are independently $C_{1-3}$alkyl, fluoro, bromo or chloro; and $R^6$ is phenyl, benzyloxy, substituted phenyl or substituted benzyloxy in which the phenyl group in each case is substituted with one or more substituents selected from $C_{1-3}$alkyl, hydroxy-$C_{1-3}$alkyl fluoro, bromo or chloro;

$R^7$ is hydrogen or $C_{1-8}$alkyl; and $R^8$ is $C_{1-8}$alkyl, hydroxy-$C_{1-8}$alkyl, phenyl-$C_{1-8}$alkyl, hydroxyphenyl-$C_{1-8}$alkyl amido-$C_{1-8}$alkyl, $C_{1-8}$alkoxy carbonyl-$C_{1-8}$alkyl, imidazol-4-yl-$C_{1-8}$alkyl, $C_{1-8}$alkylthio-$C_{1-8}$alkyl, 2-(($C_{1-8}$alkoxycarbonyl)-pyrrolidin-4-yl)-$C_{1-8}$alkyl or indol-3-yl-$C_{1-8}$alkyl;

the amido ester moiety of which is in the L-configuration of a pharmaceutically acceptable salt of the compound of the formula (I) wherein $R^7$ is hydrogen.

2. A compound of claim 1 wherein R is the group (b).

3. A compound of claim 2 wherein E is $-CH=CH-$.

4. A compound of claim 3 wherein: $R^4$ and $R^5$ independently are $C_{1-3}$alkyl; and $R^6$ is a substituted phenyl.

5. A compound of claim 4 wherein R is:

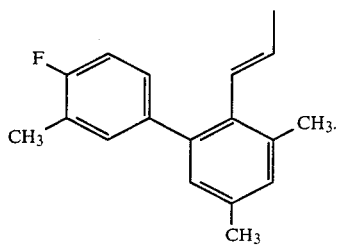

6. A compound of claim 5 wherein $R^8$ is $C_{1-8}$alkyl.

7. A compound of claim 6 which is N-[7-(4'-fluoro-3,3',5-trimethyl-[1,1'-biphenyl]-2-yl)-3(R),5(R)-dihydroxy-1-oxo-6-hepten-1-yl]-L-luecine or a pharmaceutically acceptable salt thereof.

8. A compound of claim 6 which is methyl N-[7-(4'-fluoro-3,3',5-trimethyl-[1,1'-biphenyl]-2-yl)-3(R),5(R)-dihydroxy-1-oxo-6-hepten-1-yl]-L-leucinate.

9. A compound of claim 5 wherein $R^8$ is hydroxy-$C_{1-8}$alkyl.

10. A compound of claim 9 which is N-[7-(4'-fluoro-3,3',5-trimethyl-[1,1'-biphenyl]-2-yl)-3(R),5(R)-dihydroxy-1-oxo-6-hepten-1-yl]-L-serine or a pharmaceutically acceptable salt thereof.

11. A compound of claim 9 which is methyl N-[7-(4'-fluoro-3,3',5-trimethyl-[1,1'-biphenyl]-2-yl)-3(R),5(R)-dihydroxy-1-oxo-6-hepten-1-yl]-L-serinate.

12. A compound of claim 5 wherein $R^8$ is phenyl-$C_{1-8}$alkyl.

13. A compound of claim 12 which is N-[7-(4'-fluoro-3,3',5-trimethyl-[1,1'-biphenyl]-2-yl)-3(R),5(R)-dihydroxy-1-oxo-6-hepten-1-yl]-L-phenylalanine or a pharmaceutically acceptable salt thereof.

14. A compound of claim 12 which is methyl N-[7-(4'-fluoro-3,3',5-trimethyl[1,1'-biphenyl]-2-yl)-3(R),5(R)-dihydroxy-1-oxo-6-hepten-1-yl]-L-phenylalanate.

15. A compound of claim 5 wherein $R^8$ is hydroxyphenyl-$C_{1-8}$alkyl.

16. A compound of claim 15 which is N-[7-(4'-fluoro-3,3',5-trimethyl-[1,1'-biphenyl]-2-yl)-3(R),5(R)-dihydroxy-1-oxo-6-hepten-1-yl]-L-tyrosine or a pharmaceutically acceptable salt thereof.

17. A compound of claim 1 wherein R is the group (a).

18. A hypocholesterolemic, hypolipidemic pharmaceutical composition comprising a nontoxic therapeutically effective amount of a compound of claim 1 and a pharmaceutically acceptable carrier.

19. A composition of claim 18 wherein the therapeutically active ingredient is selected from the group consisting of:
(1) N-[7-(4'-fluoro-3,3',5-trimethyl-[1,1'-biphenyl]-2-yl)-3(R),5(R)-dihydroxy-1-oxo-6-hepten-1-yl]-L-leucine;
(2) methyl N-[7-(4'-fluoro-3,3',5-trimethyl-[1,1'-biphenyl]-2-yl)-3(R),5(R)-dihydroxy-1-oxo-6-hepten-1-yl]-L-leucinate;
(3) N-[7-(4'-fluoro-3,3',5-trimethyl-[1,1'-biphenyl]-2-yl)-3(R),5(R)-dihydroxy-1-oxo-6-hepten-1-yl]-L-serine;
(4) methyl N-[7-(4'-fluoro-3,3',5-trimethyl-[1,1'-biphenyl]-2-yl)-3(R),5(R)-dihydroxy-1-oxo-6-hepten-1-yl]-L-serinate;
(5) N-[7-(4'-fluoro-3,3',5-trimethyl-[1,1'-biphenyl]-2-yl)-3(R),5(R)-dihydroxy-1-oxo-6-hepten-1-yl]-L-phenylalanine;

(6) methyl N-[7-(4'-fluoro-3,3',5-trimethyl-[1,1'-biphenyl]-2-yl)-3(R),5(R)-dihydroxy-1-oxo-6-hepten-1-yl]-L-phenylalanate;
(7) N-[7-(4'-fluoro-3,3',5-trimethyl-[1,1'-biphenyl]-2-yl)-3(R),5(R)-dihydroxy-1-oxo-6-hepten-1-yl]-L-tyrosine;
and pharmaceutically acceptable salts of (1), (3), (5) and (7).

20. A method of inhibiting cholesterol biosynthesis comprising the administration to a subject in need of such treatment a nontoxic therapeutically effective amount of a compound of claim 1.

21. A method of claim 20 wherein the therapeutically active ingredient is selected from the group consisting of:
(1) N-[7-(4'-fluoro-3,3',5-trimethyl-[1,1'-biphenyl]-2-yl)-3(R),5(R)-dihydroxy-1-oxo-6-hepten-1-yl]-L-leucine;
(2) methyl N-[7-(4'-fluoro-3,3',5-trimethyl-[1,1'-biphenyl]-2-yl)-3(R),5(R)-dihydroxy-1-oxo-6-hepten-1-yl]-L-leucinate;
(3) N-[7-(4'-fluoro-3,3',5-trimethyl-[1,1'-biphenyl]-2-yl)-3(R),5(R)-dihydroxy-1-oxo-6-hepten-1-yl]-L-serine;
(4) methyl N-[7-(4'-fluoro-3,3',5-trimethyl-[1,1'-biphenyl]-2-yl)-3(R),5(R)-dihydroxy-1-oxo-6-hepten-1-yl]-L-serinate;
(5) N-[7-(4'-fluoro-3,3',5-trimethyl-[1,1'-biphenyl]-2-yl)-3(R),5(R)-dihydroxy-1-oxo-6-hepten-1-yl]-L-phenylalanine;
(6) methyl N-[7-(4'-fluoro-3,3',5-trimethyl-[1,1'-biphenyl]-2-yl)-3(R),5(R)-dihydroxy-1-oxo-6-hepten-1-yl]-L-phenylalanate;
(7) N-[7-(4'-fluoro-3,3',5-trimethyl-[1,1'-biphenyl]-2-yl)-3(R),5(R)-dihydroxy-1-oxo-6-hepten-1-yl]-L-tyrosine;
and pharmaceutically acceptable salts of (1), (3), (5) and (7).

* * * * *